(12) United States Patent
Bunker et al.

(10) Patent No.: US 6,804,622 B2
(45) Date of Patent: Oct. 12, 2004

(54) METHOD AND APPARATUS FOR NON-DESTRUCTIVE THERMAL INSPECTION

(75) Inventors: Ronald Scott Bunker, Niskayuna, NY (US); Nirm Velumylum Nirmalan, Niskayuna, NY (US); Louis Andrew Schick, Delmar, NY (US)

(73) Assignee: General Electric Company, Niskayuna, NY (US)

( * ) Notice: Subject to any disclaimer, the term of this patent is extended or adjusted under 35 U.S.C. 154(b) by 116 days.

(21) Appl. No.: 09/945,990

(22) Filed: Sep. 4, 2001

(65) Prior Publication Data

US 2003/0055594 A1 Mar. 20, 2003

(51) Int. Cl.$^7$ .......................... G06F 15/00; G01N 25/20
(52) U.S. Cl. .................... 702/134; 73/204.23; 324/752; 374/43
(58) Field of Search .................... 702/49, 134, 135, 702/136; 374/29, 30, 31, 43, 44; 73/204.23; 250/330, 340

(56) References Cited

U.S. PATENT DOCUMENTS

| | | | | |
|---|---|---|---|---|
| 4,067,237 A | * | 1/1978 | Arcella | 73/204.23 |
| 4,621,929 A | * | 11/1986 | Phillips | 374/43 |
| 4,644,162 A | | 2/1987 | Bantel et al. | 250/340 |
| 4,896,281 A | * | 1/1990 | Mack | 702/134 |
| 5,111,046 A | | 5/1992 | Bantel | 250/330 |
| 6,422,743 B1 | * | 7/2002 | Nirmalan et al. | 374/43 |

OTHER PUBLICATIONS

US 2002/0011852 A1, Mandelis et al., Pub. Date: Jan. 31, 20002, FiledDate: Mar. 21, 2001, "Non–contact photothermal radiometric metrologies and characterization of semiconductor wafers, device and non electronic materials".*

Thermosense XVIII: An International Conference on Thermal Sensing and Imaging Diagnostic Applications, "Nondestructive Pulsed Infared Quantitative Evaluation of Metals", Arnold Daniels, Apr. 10, 12, 1996, Orlando, Florida, vol. 2766, pps. 185201.

"Thermography Inspection System for Gas Turbine Blades", 7th ECNDT, Copenhagen, May 1998, 8 pages"The Thermal Inertia Analysis Technique in Gas Turbine Component Reliability Assessment", J. Stiglich, Jr.,et al. Oct. 12–15, 1998, 14 pgs.

"A Transient Liquid Crystal Mthod Using Hue Angle and a 3–D Inverse Transient Conduction Scheme", M. Lin, T. Wang, Proceedings of ASME Turboexpo 2000, May 8–11, 2000, Munich, Germany, pp. 1–7.

"The Thermal Inertia Analysis Technique in Gas Turbine Component Reliability Assessment", J. Stiglich, Jr., CC Bishop, J.A. Daleo, D.H. Boone, T.E. Eelkema, ASM Gas Turbines Materials Technology Conference, Oct. 12–15, 1998.

* cited by examiner

Primary Examiner—John Barlow
Assistant Examiner—John H Le
(74) Attorney, Agent, or Firm—Patrick K. Patnode; Christian G. Cabou

(57) ABSTRACT

A method of quantitative non-destructive thermal inspection of an article having at least one internal cavity comprises the steps of inputting physical properties of the article, measuring thermal characteristics of the article, and calculating heat transfer coefficients of the internal cavity.

33 Claims, 3 Drawing Sheets

_US 6,804,622 B2_

METHOD AND APPARATUS FOR NON-DESTRUCTIVE THERMAL INSPECTION

BACKGROUND OF THE INVENTION

The present invention relates generally to thermal inspection methods and apparatus and, more particularly, to non-destructive thermal inspection methods and apparatus.

Currently, most internally cooled components are inspected by various techniques using flow checks, dimensional gauges and other visual methods. Industry typically relies on these methods to determine the quality (pass/fail) of each part as compared to a nominal standard part or a specification. In this practice there is no quantitative way to distinguish between two parts that may have very different internal thermal performance, but which flow the same amount and otherwise pass all external dimensional tests.

Accordingly, there is a need in the art for an improved method of thermal inspection and specifically, there is a need for a quantitative non-destructive thermal inspection method and apparatus.

BRIEF SUMMARY OF THE INVENTION

A method of quantitative non-destructive thermal inspection of an article having at least one internal cavity comprises the steps of inputting physical properties of the article, measuring thermal characteristics of the article, and calculating heat transfer coefficients of the internal cavity.

DETAILED DESCRIPTION OF THE INVENTION

Figure 1:
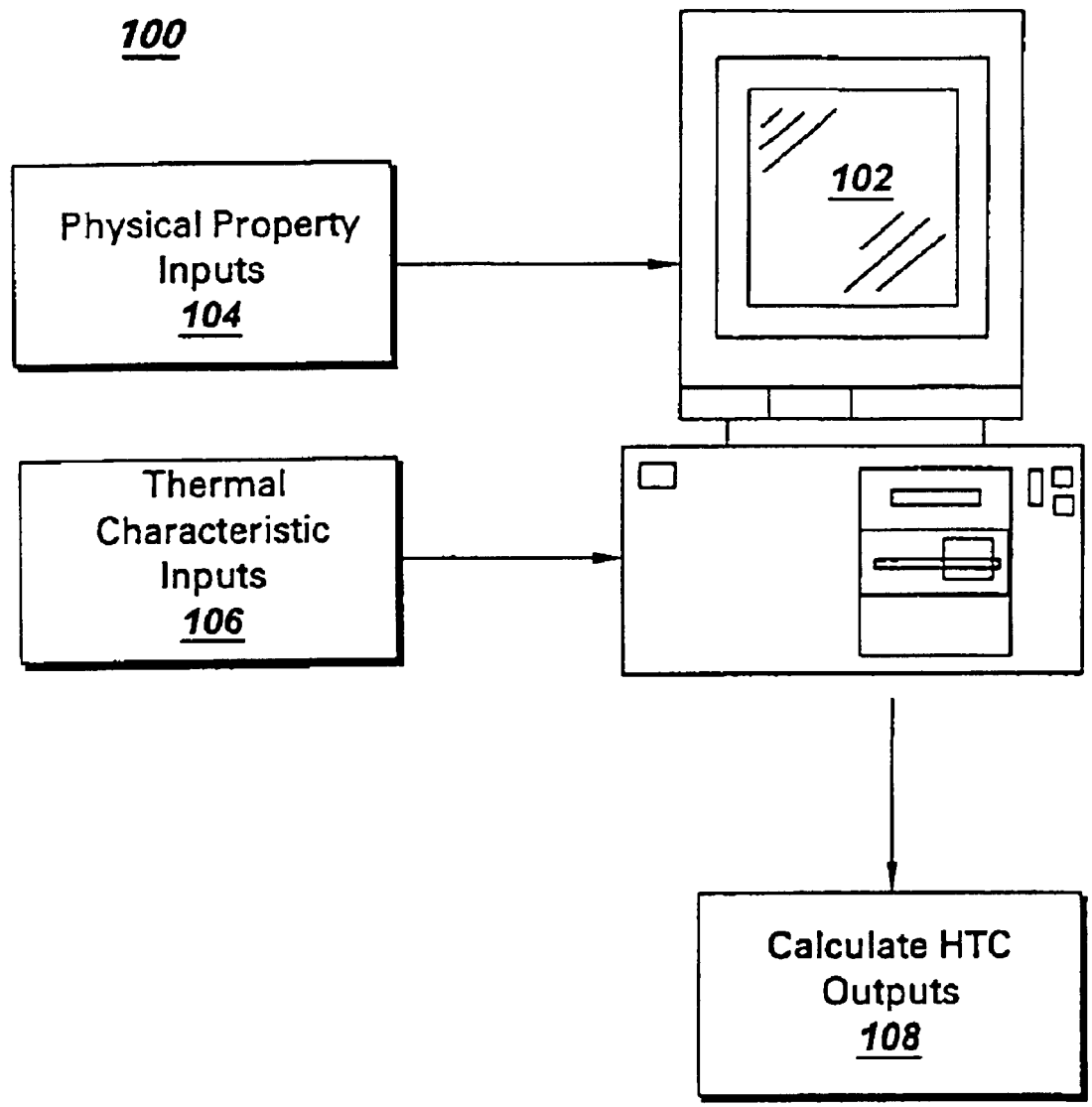
FIG. 1 is schematic illustration of an inspection system in accordance with one aspect of the invention.
Figure 2:
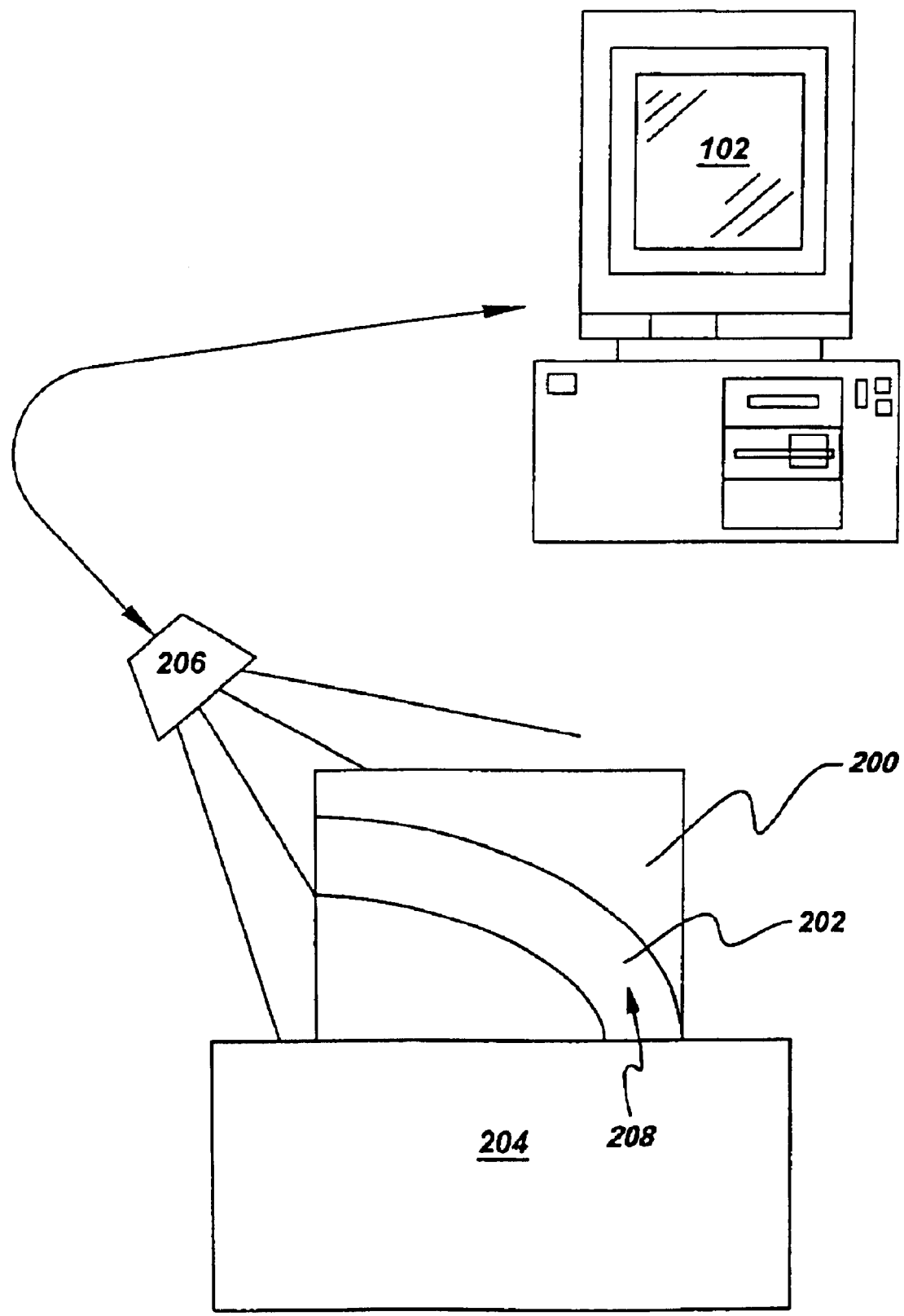
FIG. 2 is schematic illustration of an inspection system in accordance with another aspect of the invention.
Figure 3:
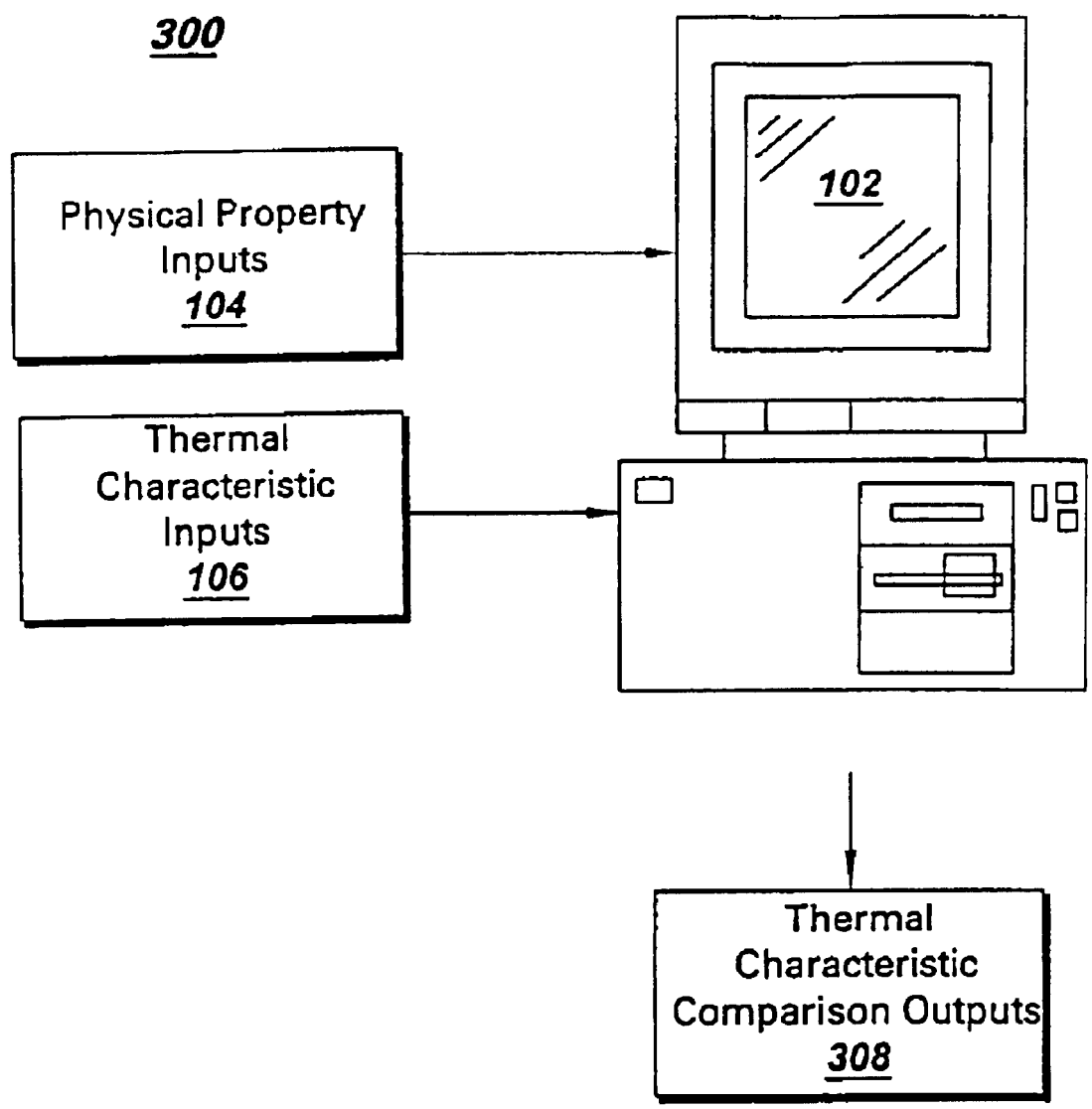
FIG. 3 is schematic illustration of an inspection system in accordance with another aspect of the invention.

As used herein, the term "Computer" means a programmable device that responds to a specific set of instructions. A computer can be electronic or digital. The actual machinery, for example, wires, transistors, and circuits is called hardware and the instructions are called software. Most computers typically comprise: a memory that enables a computer to store, at least temporarily, data and programs; a mass storage device that allows a computer to permanently retain large amounts of data (common mass storage devices include disk drives and tape drives); an input device, for example, a keyboard or mouse, through which data and instructions enter a computer; an output device for example a display, screen or printer or other device that lets you see what the computer has accomplished; and a central processing unit (CPU), the component that executes instructions. In addition to these components, many other components make it possible for the basic components to work together efficiently. For example, most computers have a bus that transmits data from one part of the computer to another. Some examples of typical computers are a personal computer, a workstation, a minicomputer, multi-user computer, a mainframe, or a supercomputer.

As used herein, the term "Cavity" means any type of internal flow area including small diameter channels or large volume spaces including any type of geometry, for example a serpentine cooling path or the like. The common feature is that cavities are capable of fluid flow within.

As used herein, the term "Database" means a collection of organized data. The data is typically organized for rapid search and retrieval by a computer.

As used herein, the term "Internet" means a global network of computers.

As used herein, the term "Intranet" means a secure network, typically belonging to an organization, for example, a corporation, accessible only by that organization's members, employees, or others with appropriate authorization, for storage and sharing of information.

As used herein, the term "Media" means at least one of a RAM, A ROM, a disk, a DVDROM, a CDROM, an ASIC, a PROM, or any other type of storage means.

As used herein, the term "Network" means a group of two or more computers linked together. There are many types of networks, including: local-area networks (LANs), where the computers are geographically close together, typically, in the same building, and wide area networks (WANs) where the computers are farther apart and are connected by telephone lines or radio waves. In addition to these types, the following characteristics are also used to categorize different types of networks: topology is the geometric arrangement of a computer system (common topologies include a bus, a star, and a ring); the protocol defines a common set of rules and signals that computers on the network use to communicate (one of the most popular protocols for LANs is called Ethernet). Networks can be broadly classified as using either a peer-to-peer or client/server architecture. Computers on a network are sometimes called nodes. Computers and devices that allocate resources for a network are called servers.

A schematic of a quantitative non-destructive thermal inspection system 100 for inspection of articles having internal cooling cavities is shown in FIG. 1. Certain parts or all of system 100 may be embedded in the form of algorithms in a computer 102. The algorithm can be programmed in C, C++, JAVA, Basic, MATLAB, Visual Basic, Fortran, or any other programming language.

System 100 comprises computer 102, physical property inputs 104 and thermal characteristic inputs 106. Computer 102 then uses these inputs to calculate heat transfer coefficient (HTC) outputs 108. This method quantifies internal heat transfer coefficients of as-made articles and does not rely upon a comparison against a specification or nominal standard part for determination of the internal heat transfer coefficients. This method is a self-standing technique, capable of determining the heat transfer of an internally cooled article.

Physical property inputs 104 include multiple inputs about an article identified for non-destructive thermal inspection. The physical properties of the article include the wall thickness (x, y, z), specific heat and density. Estimates can be used with each of these inputs. The accuracy of the result, however, will be affected by resolution of the input data.

Article wall thickness varies with location in a typical article, sometimes continuously as in the hub-to-tip variation of a turbine blade. Occasionally, the thickness varies in discrete steps as in the case of internal ribs or turbulators of a turbine blade. Knowledge of the actual wall thickness is necessary to discern the local internal heat transfer coefficient from the response of the local external temperatures. A nominal 3D geometry can be known from the drawings or specifications of the article or from a CAD drawing, for example a Unigraphics™ file. In order for the drawings, specification or CAD drawing to be acceptable within the instant process, the tolerances on the drawing must be tight or the sensitivity of the resultant internal heat transfer coefficients to variation in the wall thickness must be small.

Alternatively, another method of quantifying wall thickness is with an X-ray system, however, this system requires many exposures to achieve high levels of accuracy within all regions of the article. Ultrasound systems can be utilized as well, but this process would take very long inspection periods.

In another embodiment, transient Infrared Imaging is used to quantify wall thickness of an article. In this method, an intense flash of radiative energy heats a surface, for example using flash lamps. The radiative energy penetrates to different depths in different times, thereby affecting the external IR surface temperature detected. The time evolution of the surface temperature at each location can be analyzed, and with knowledge of certain material properties, the wall thickness can be determined. This method operates with a transient thermal pulse on the order of milli-seconds and a surface response time on the order of seconds. This method is capable of discerning local wall thickness to between about ±0.02 inches to about ±0.002 inches.

Thermal characteristic inputs 104 typically involves measuring the change of external surface temperature over time of an article when presented with a thermal transient via an introduced fluid flow, and capturing these temperature changes in computer 102.

In one embodiment, an article 200 having an internal cooling cavity 202 is positioned on a flow stand 204. A camera device 206, coupled to a computer, for example computer 102, is positioned adjacent article 200 to capture image data related to the external surface temperatures of article 200.

Typically camera device 206 is an Infrared camera. Computer 102 is typically capable of capturing an image frame rate of adequate frequency, for example greater than 10 frames per second and typically greater than 15 frames per second, from camera device 206. The temperature-time history of the external surface of article 200 is readily measured by the use of the camera device 206 and computer 102. The temperature-time history of each location on the external surface is recorded in computer 102 for analysis. The detailed measurement of the external surface temperature distribution is dependent on the resolution of the camera device 206, i.e. the density of the pixel array in the device.

Infrared camera device 206 is typically calibrated for surface emissivity ($\epsilon$). This can be completed by using black paint of known emissivity on the surface of the article 200 or by using a coating with a known emissivity. Alternatively, the Infrared camera device 206 can also be calibrated using thermocouples. Additionally, background sources of radiation should be eliminated or minimized for system accuracy.

Article 200 is then heated or cooled to an initial starting temperature, or temperature distribution, that is measured. A thermal cover, lamps, induction or the like can be used to heat the article 200. A refrigeration cover or the like can be used to cool the article 200. Alternatively, the article 200 can be heated or cooled by an internal fluid flow 208, for example hot or cool water or air.

At time t=0, the heating or cooling of article 200 is stopped and the temperature (T) of the article is measured and stored in computer 102. Next, an internal steady flow 208 is introduced from flow stand 204 into internal cooling cavity 202. The external surface of the article 200 is imaged using the Infrared camera device 206 and the associated external surface temperatures are recorded as a function of time t>0 in computer 102. The actuation of flow 208 can be sudden or gradual, but the flow rate must remain substantially steady during the time period of usable data. Steady flow rate is understood as a constant or nearly constant rate of flow, with steady inlet pressure. The magnitude of fluctuations in the flow rate will contribute to the uncertainty of the results. Typically, the initial temperature difference between the article 200 and the fluid flow 208 should be in the range between 200F to about 400F and preferably between 250F to about 350F (prior to imaging).

If an article 200 is heated to a known temperature, then a cooling transient 208 is initiated by the introduction of a cool fluid flow 208 to the internal cavity 202 of the article 200. Alternatively, if an article 200 is cooled to a known temperature, then a heating transient is initiated by the introduction of a heated flow 208 to the internal cavity 202 of the article 200.

As discussed above, Infrared Imaging is not the only means of detecting surface temperatures. A video system could be used with thermographic phosphor coating on the article 200. In this embodiment, article 200 is covered in a temperature sensitive coating, for example a thermographic phosphor, and the change in the emitted wavelength magnitudes of the external surface of the article 200 is captured via detector device 206, for example a UV imaging system, and stored in computer 102. As known, when using a thermographic phosphor, an excitation source, for example a laser (not shown) is used to excite the coating and UV imaging system is used to capture the excitation. In another embodiment, camera device 206 is a visible light imaging system. The visible light imaging system is typically used with a liquid crystal coating, or temperature indicating paint, on article 200.

Next, computer 102 calculates the HTC's of the internal cavity 202 of the article 200 by using measured, assumed, or derived internal coolant temperatures within the flow circuit. The internal heat transfer coefficient (h) is computed for each location on the article using a one-dimensional lumped thermal capacity method:

$$\frac{Tw(\text{final}) - Tw(t)}{Tw(\text{final}) - Tw(t=0)} = e^{-at} \text{ and}$$

$$a = \frac{h}{\rho l C_p};$$

where $T_w$ is the internal temperature of the wall, a is the thermal capacitance coefficient, h is the heat transfer coefficient, $\rho$ is the material density, l is the thickness, and $C_p$ is the specific heat. A linear T(t) fit or a curve fit for T(t) at each location on article may be used. In this initial approximation, $T_w$ is assumed to be equal to $T_s$, the external surface temperature.

Once this step is completed, the internal heat transfer coefficients are known for each location on the article 200. With the heat transfer coefficients, this method has quantified internal heat transfer coefficients of as-made articles. These results can be used to thermally inspect articles in a non-destructive manner.

If an article is simple, then the heat transfer coefficients as determined by a one-dimensional lumped thermal conduction solution is sufficient. If no flow circuit model is present, a flow model may be replaced by a simple fixed distribution of fluid temperatures. Furthermore, if the wall thickness of an article is of constant thickness, then no IR Flash measurement is required.

Additionally, the local temperature-time history of the part to determine an internal heat transfer coefficient can use a one dimensional lumped thermal conduction model and subsequent use of the transient surface temperatures can be performed in a variety of ways. A three dimensional inverse conduction model can be executed to arrive at a part thermal condition at some specified point in time and then compared this to the measured condition.

Certain follow-on or enhancements to the calculated heat transfer coefficients can be done to increase accuracy of the results. Using the first approximations for the HTC's, there is no knowledge or correction for internal two-dimensional and three-dimensional structures and no data or corrections for heat exchange between the fluid and internal walls that can cause spatial and temporal variations in the local fluid temperatures. The initial wall thickness assumption fails to account for the internal structures or ribs. Additionally, the calculations do no account for neighbor to neighbor heat transfer, i.e. heat transfer between one discrete section of article 200 and a neighboring discrete section.

A correction of the heat transfer based on the thickness of the wall can be made using the following equations:

$$q/A_M = -K\frac{\Delta T}{\Delta X}; \text{Fourier's Law of Thermal Conduction}$$

$$\frac{q}{A_w} = h(T_w - T_{fl}); \text{and}$$

$$\Delta T_{wall} = \frac{q\Delta X}{AK}; \text{where}$$

$q/A_M$ is the heat flux per unit area through the wall material, K is the thermal conductivity, $\Delta T$ is the temperature change, $\Delta X$ is the wall thickness, $A_W$ is the internal surface area, h is the initial heat transfer coefficient, $T_w$ is the temperature of the Internal wall and $T_{fl}$ is the temperature of the working fluid. These equations correct for the initial assumption that $T_w=T_s$. After the $\Delta T_{wall}$ value is calculated, the initial h estimates are corrected using the new more accurate data.

Next, another correction can be made for lateral conduction. Using known $T_w$ and estimated $T_s$ the center point for each discrete section of the article is calculated. Lateral heat flux corrections are then made using Fourier's Law and new estimates for $T_w$ are made. These calculations are then incorporated into a more refined estimate to produce h for each location.

An energy balance can be applied to the fluid flow temperature to obtain local internal coolant temperatures. The initial solution for heat transfer coefficients can be used to perform this energy balance. Improved heat transfer coefficients will result when the 1D or 3D analysis is updated. Computing local temperatures of the working fluid typically involves inputting measured temperatures over time, at one or more locations, and estimating the local temperatures using the measured temperatures based on a circuit flow and energy transfer model. Component cooling circuit, whether simple once-through systems or complex multi-pass systems, are typically modeled by one-dimensional flow networks of incompressible or compressible flows. A network flow modeling tool is provided with the supply pressure and temperature of the fluid flow and the exit point pressure and temperature of the fluid flow, as well as information about effective flow areas, discharge coefficients, orifices, and friction/pressure loss data or correlations. The model is then able to compute the local fluid conditions and flow rates at any desired point within the component. In one embodiment, the network flow-modeling tool is Flowmaster™ or the like, for example, any commercially available computational fluid dynamics software that is capable of modeling internal flow conditions.

Additionally, the transient data and assumed/known conditions can be applied to a Finite Element Model of the part or portion thereof. Conduction FEM models are utilized within industry. Many third party software applications, for example ANSYS™, are available to build and execute these models. The usual practice is to grid a 3D model of a part for a solution of the transient energy equation. The required inputs for such a model are the geometry, material properties, and both the internal and external thermal boundary conditions, (the local fluid temperatures and local heat transfer coefficients). Zero heat flux external boundary conditions or a known/estimated external surface heat transfer coefficient and external fluid temperature can also be used.

The typical output of a model is the temperature of the part at each location. Alternatively, such a FEM can be used in an iterative manner with the temperatures of the part and fluid as inputs, to determine the heat transfer coefficients. A two-dimensional or three-dimensional inverse transient conduction model can be solved for the actual part geometry, using the one-dimensional solution as the initial estimate. First, the solution compares calculated T to one-dimensional solution (compares the local external surface temperatures). The internal heat transfer coefficients are updated using a method such as Newton's Method for root finding and convergence continues until a desired accuracy level or convergence criteria is obtained. The internal energy balance is updated using the new flow network model and the final heat transfer solutions are identified.

In another embodiment of the instant invention, a system 300 comprises computer 102, physical property inputs 104 and thermal characteristic inputs 106. Computer 102 then uses these inputs to compare the thermal characteristic inputs to baseline thermal characteristics and produces thermal characteristic comparison output 308. The thermal characteristic comparison output 308 is then used to accept, reject or categorize the article.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method of quantitative non-destructive thermal inspection of a three-dimensional article having at least one three-dimensional internal cavity comprising the steps of:

inputting physical properties of said article, wherein said physical properties comprise three-dimensional parameters;

measuring thermal characteristics of said article; and calculating heat transfer coefficients of said at least one three-dimensional internal cavity, wherein said calculating heat transfer coefficients accounts for said three-dimensional parameters.

2. A method in accordance with claim 1, wherein the step of measuring thermal characteristics of said article comprises:

providing an article at a known T;

providing a working fluid to said internal cavity of said article; and measuring the external surface temperature of said article over time.

3. A method in accordance with claim 2, wherein providing an article at a predetermined T comprises providing a heated article.

4. A method in accordance with claim 2, wherein providing an article at a predetermined T comprises providing a cooled article.

5. A method in accordance with claim 2, wherein measuring the surface temperature of said article over time is completed using an IR system.

6. A method in accordance with claim 2, wherein measuring the surface temperature of said article over time is completed by coating said article with temperature sensitive material and using a visible imaging system.

7. A method in accordance with claim 1, wherein said step of computing local temperatures of a working fluid comprises inputting measured temperatures over time and estimating said local temperatures using said measured temperatures based on the circuit flow model.

8. A method in accordance with claim 1, wherein the step of inputting physical properties includes inputting at least one of article geometry, article wall thickness, article surface emissivity, article thermal conductivity, article specific heat, and article density.

9. A method of determining internal HTC's of a three-dimensional article having at least one three-dimensional internal cavity comprising the steps of:
    measuring thermal characteristics of said article;
    computing local temperatures of a working fluid introduced within said at least one internal cavity;
    inputting physical properties of said article, wherein said physical properties comprise three-dimensional parameters; and
    calculating heat transfer coefficients of said at least one three-dimensional internal cavity, wherein said calculating heat transfer coefficients accounts for said three-dimensional parameters.

10. A method in accordance with claim 9, wherein the step of measuring thermal characteristics of said article comprises:
    providing an article at a known T;
    measuring the surface temperature of said article over time;
    providing a working fluid to said internal cavity of said article; and
    measuring the working fluid temperature over time.

11. A method in accordance with claim 10, wherein providing an article at a predetermined T comprises providing a heated article.

12. A method in accordance with claim 10, wherein providing an article at a predetermined T comprises providing a cooled article.

13. A method in accordance with claim 10, wherein measuring the surface temperature of said article over time is completed using an IR system.

14. A method in accordance with claim 10, wherein measuring the surface temperature of said article over time is completed by coating said article with temperature sensitive material and using a visible imaging system.

15. A method in accordance with claim 9, wherein said step of computing local temperatures of a working fluid comprises inputting measured temperatures over time and estimating said local temperatures using said measured temperatures based on the circuit flow model.

16. A method in accordance with claim 9, wherein the step of inputting physical properties includes inputting at least one of article geometry, article wall thickness, article surface emissivity, article thermal conductivity, article specific heat, and article density.

17. A method of non-destructive thermal inspection comprising the steps of:
    inputting physical properties of an article, wherein said physical properties comprise three-dimensional parameters;
    measuring thermal characteristics of said article; and
    comparing said thermal characteristics of said article to baseline thermal characteristics.

18. A method in accordance with claim 17, wherein said inputting physical properties of said article includes inputting at least one of article geometry, article wall thickness, article surface emissivity, article thermal conductivity, article specific heat, article density, and article thermal diffusivity.

19. A method in accordance with claim 17, wherein the step of measuring thermal characteristics of said article comprises:
    providing an article at a predetermined T;
    measuring the surface temperature of said article over time;
    providing a working fluid to said article; and
    measuring the working fluid temperature over time.

20. A method in accordance with claim 19, wherein providing an article at a predetermined T comprises providing a heated article.

21. A method in accordance with claim 19, wherein providing an article at a predetermined T comprises providing a cooled article.

22. A method in accordance with claim 19, wherein measuring the surface temperature of said article over time is completed using an IR imaging system.

23. A method in accordance with claim 19, wherein measuring the surface temperature of said article over time is completed by cooling said article with temperature sensitive material and using a visible imaging system.

24. A method in accordance with claim 17, further comprising the step of utilizing the comparison of said measured thermal characteristics and said baseline thermal characteristics to accept, reject or categorize said article.

25. Computer-readable media tangibly embodying a program of instructions executable by a computer to perform a method of quantitative non-destructive thermal inspection of a three-dimensional article having at least one three-dimensional internal cavity comprising the steps of:
    inputting physical properties of said article, wherein said physical properties comprise three-dimensional parameters;
    measuring thermal characteristics of said article; and
    calculating heat transfer coefficients of said at least one three-dimensional internal cavity.

26. Computer-readable media tangibly embodying a program of instructions in accordance with claim 25, wherein the step of measuring thermal characteristics of said article comprises:
    providing an article at a known T;
    providing a working fluid to said internal cavity of said article; and
    measuring the external surface temperature of said article over time.

27. Computer-readable media tangibly embodying a program of instructions in accordance with claim 26, wherein providing an article at a predetermined T comprises providing a heated article.

28. Computer-readable media tangibly embodying a program of instructions in accordance with claim 26, wherein providing an article at a predetermined T comprises providing a cooled article.

29. Computer-readable media tangibly embodying a program of instructions in accordance with claim 26, wherein measuring the surface temperature of said article over time is completed using an IR system.

30. Computer-readable media tangibly embodying a program of instructions in accordance with claim 26, wherein measuring the surface temperature of said article over time is completed by coating said article with temperature sensitive material and using a visible imaging system.

31. Computer-readable media tangibly embodying a program of instructions in accordance with claim 25, wherein said step of computing local temperatures of a working fluid comprises inputting measured temperatures over time and estimating said local temperatures using said measured temperatures based on the circuit flow model.

32. Computer-readable media tangibly embodying a program of instructions in accordance with claim 25, wherein the step of inputting physical properties includes inputting at least one of article geometry, article wall thickness, article surface emissivity, article thermal conductivity, article specific heat, and article density.

33. Computer-readable media tangibly embodying a program of instructions in accordance with claim 25, wherein said media comprise a RAM, A ROM, a disk, a DVDROM, a CDROM, an ASIC, and a PROM.

* * * * *